(12) United States Patent
Reuben

(10) Patent No.: US 8,372,128 B2
(45) Date of Patent: Feb. 12, 2013

(54) SELF ADHESIVE BANDAGE EMBODYING LIGHT INFUSED PHOTODYNAMICALLY SANITIZED PERMEABLE ABSORBENT PAD OUTER SURFACE

(76) Inventor: David Isidore Reuben, Las Vegas, NV (US)

( * ) Notice: Subject to any disclaimer, the term of this patent is extended or adjusted under 35 U.S.C. 154(b) by 0 days.

(21) Appl. No.: 13/410,126

(22) Filed: Mar. 1, 2012

(65) Prior Publication Data
US 2012/0165716 A1 Jun. 28, 2012

Related U.S. Application Data

(63) Continuation of application No. 11/426,061, filed on Aug. 30, 2006, now abandoned.

(51) Int. Cl.
*A61N 5/06* (2006.01)
(52) U.S. Cl. .......................................................... 607/88
(58) Field of Classification Search ............... 607/88–94
See application file for complete search history.

(56) References Cited

U.S. PATENT DOCUMENTS

| | | | | |
|---|---|---|---|---|
| 4,416,075 A | * | 11/1983 | Bauer | 40/546 |
| 4,902,278 A | * | 2/1990 | Maget et al. | 604/132 |
| 6,331,111 B1 | * | 12/2001 | Cao | 433/29 |
| 2006/0173514 A1 | * | 8/2006 | Biel et al. | 607/88 |

* cited by examiner

*Primary Examiner* — Aaron Roane

(57) ABSTRACT

A Band-Aid type self-adhesive bandage whose absorbent pad outer surface is photodynamically sanitized while maintaining standard absorbency performance.

20 Claims, 12 Drawing Sheets

SELF ADHESIVE BANDAGE EMBODYING LIGHT INFUSED PHOTODYNAMICALLY SANITIZED PERMEABLE ABSORBENT PAD OUTER SURFACE

CROSS REFERENCE TO RELATED APPLICATIONS

This is a continuation of application Ser. No. 11/426,061 filed Aug. 30, 2006, now abandoned.

DRAWINGS

Figures

Figure 1:
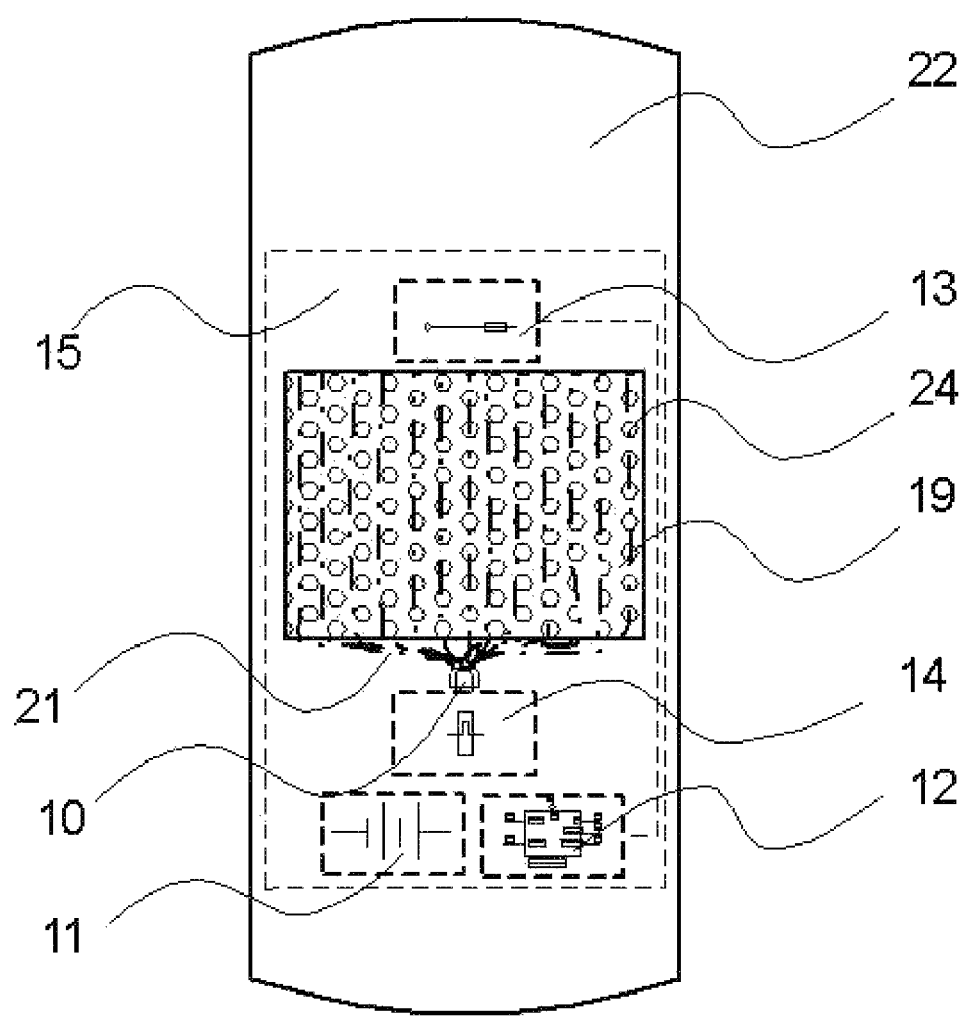
Figure 2:
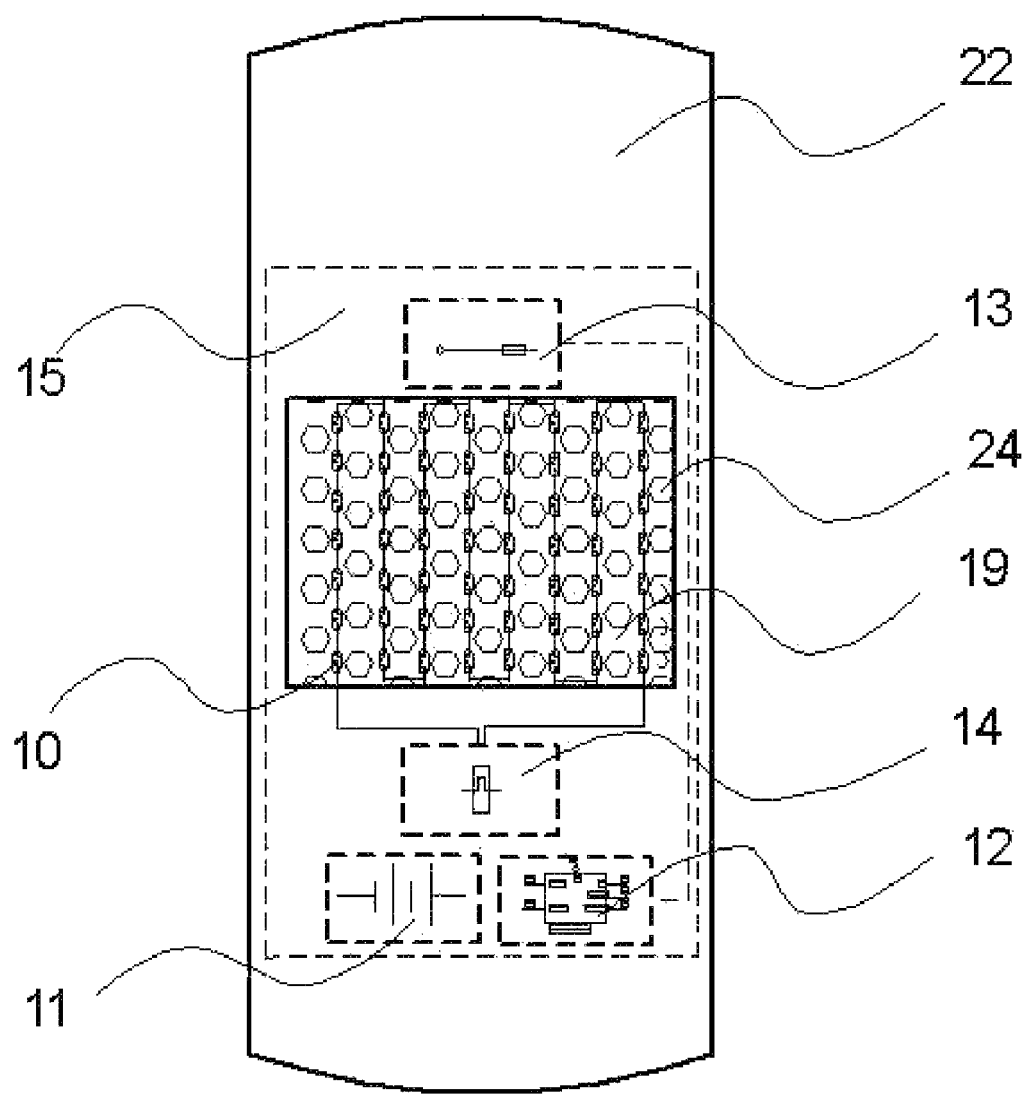
Figure 3:
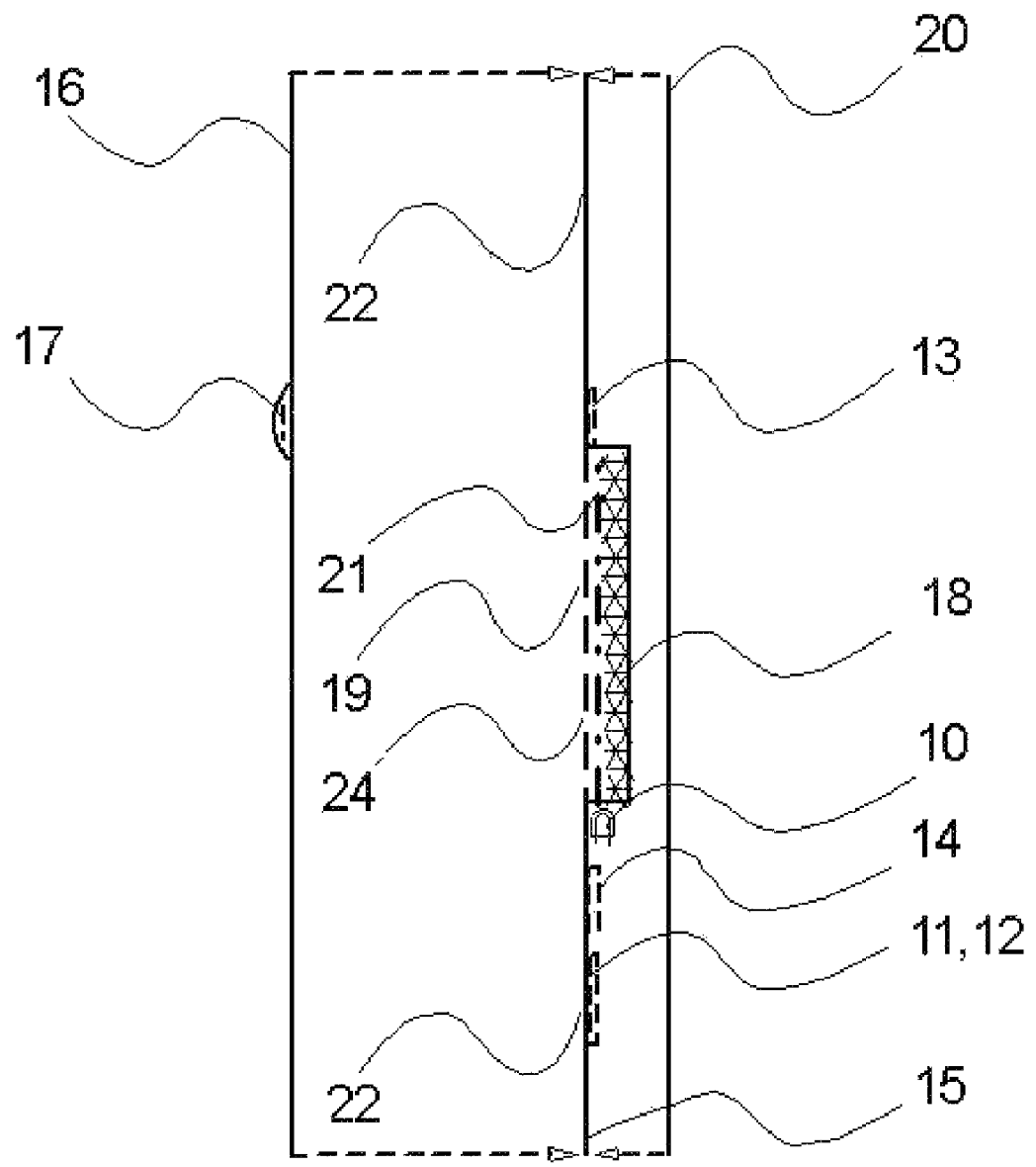
Figure 4:
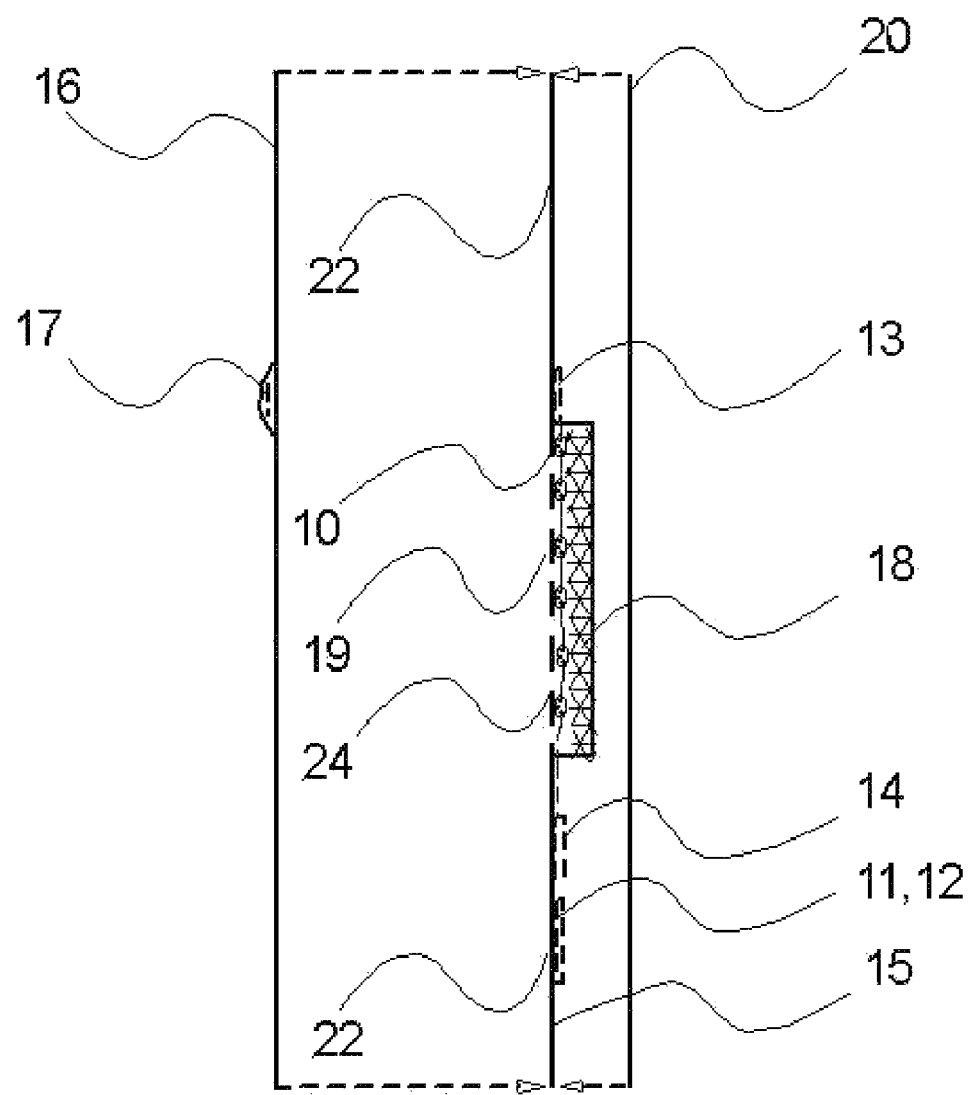
Figure 5:
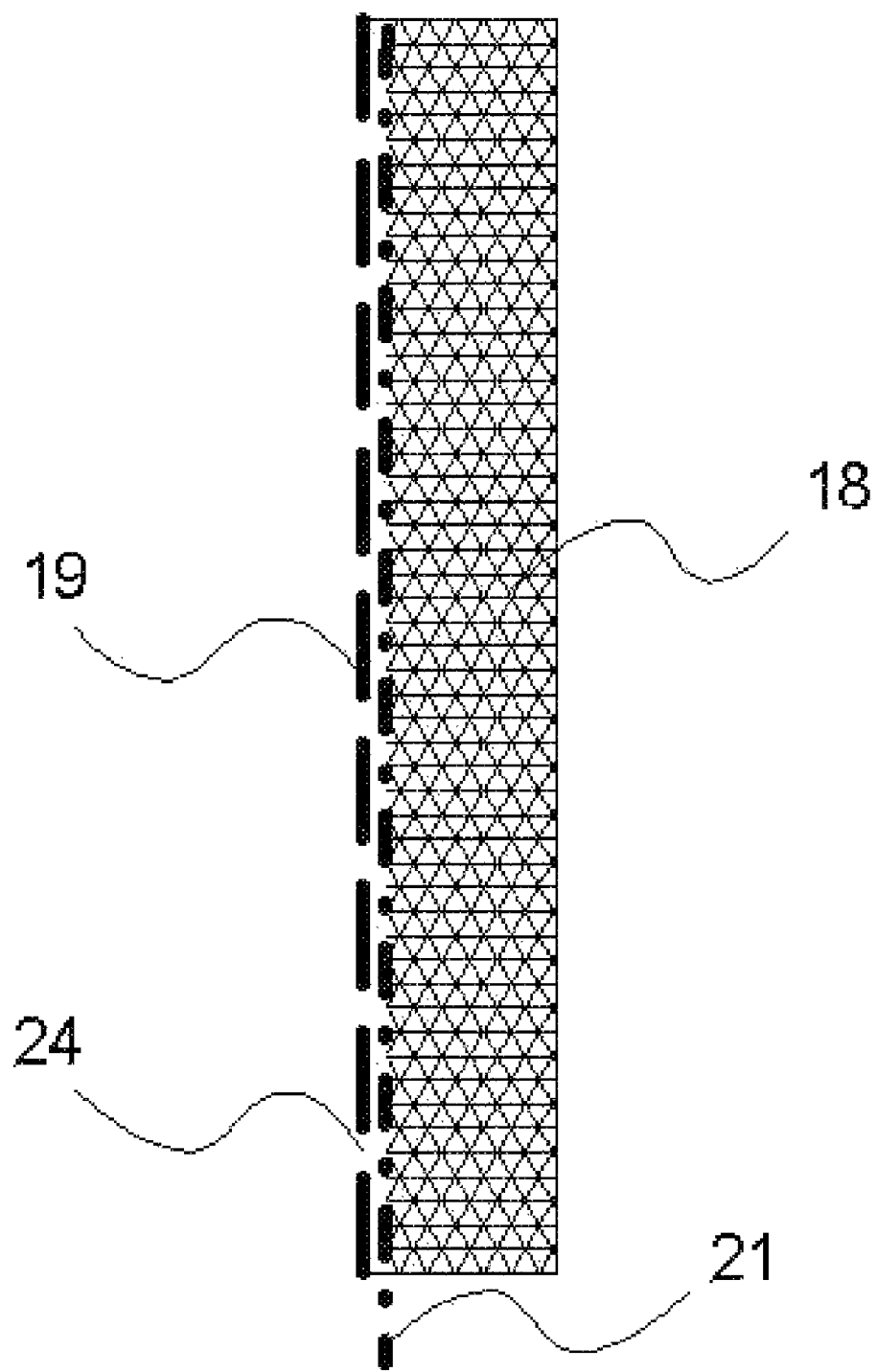
Figure 6:
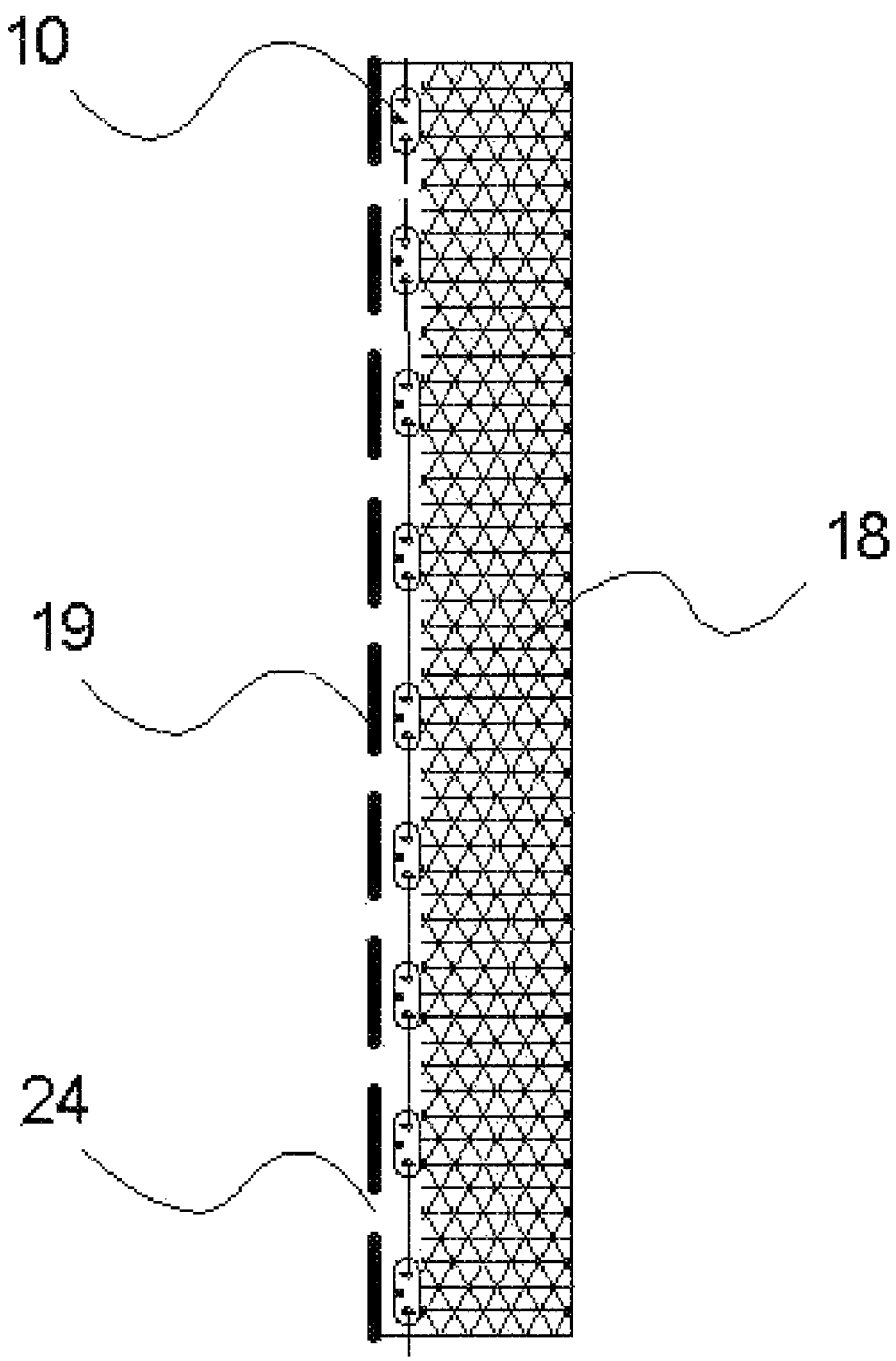
Figure 7:
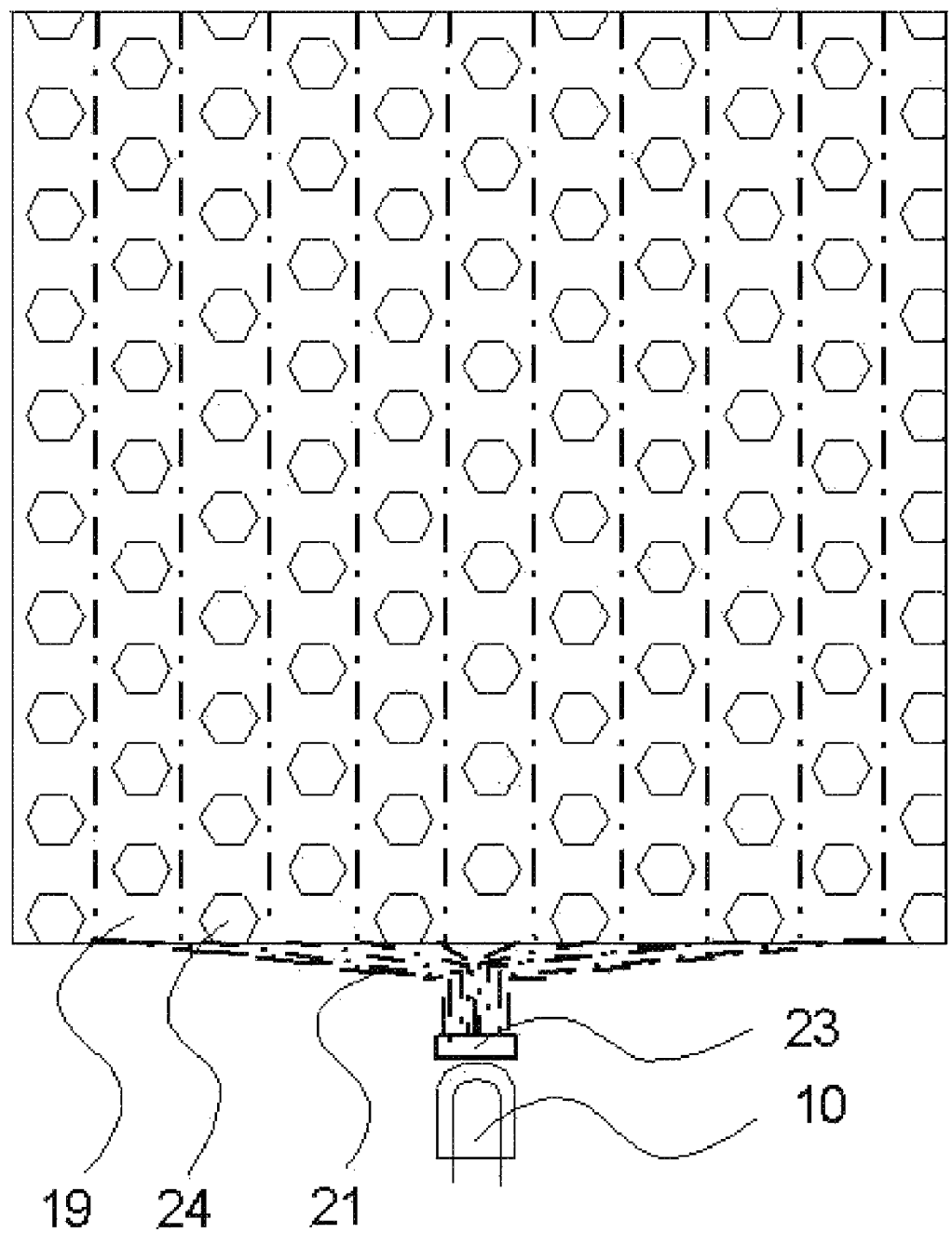
Figure 8:
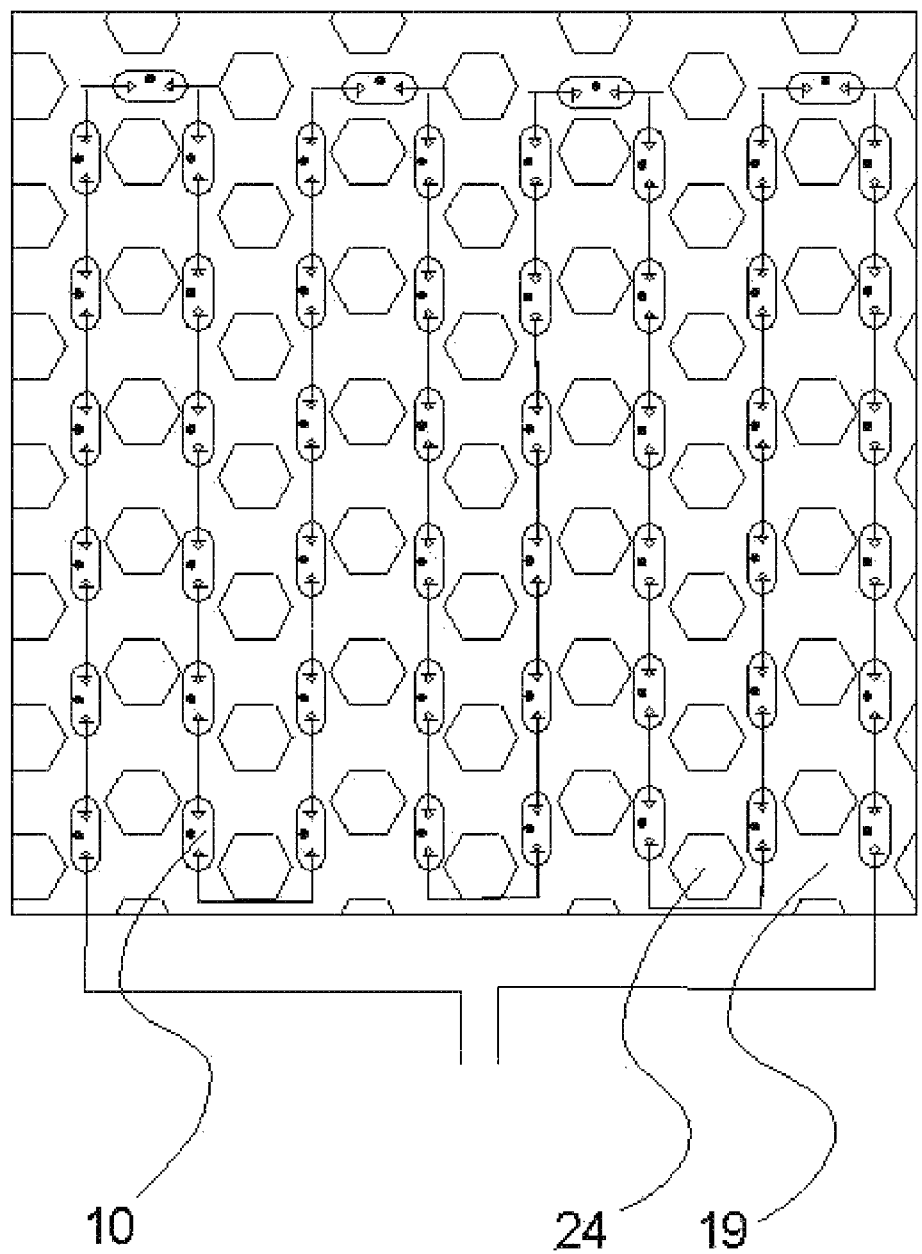
Figure 9:
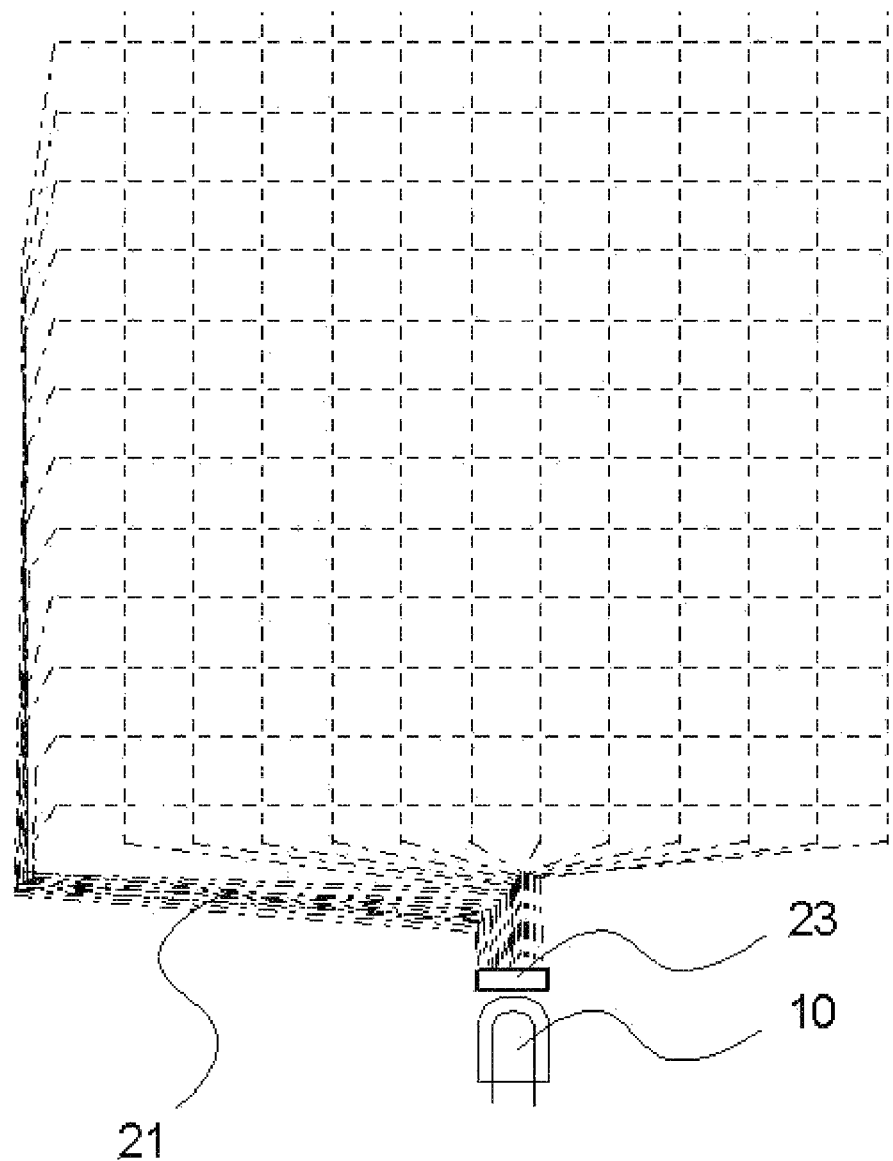
Figure 10:
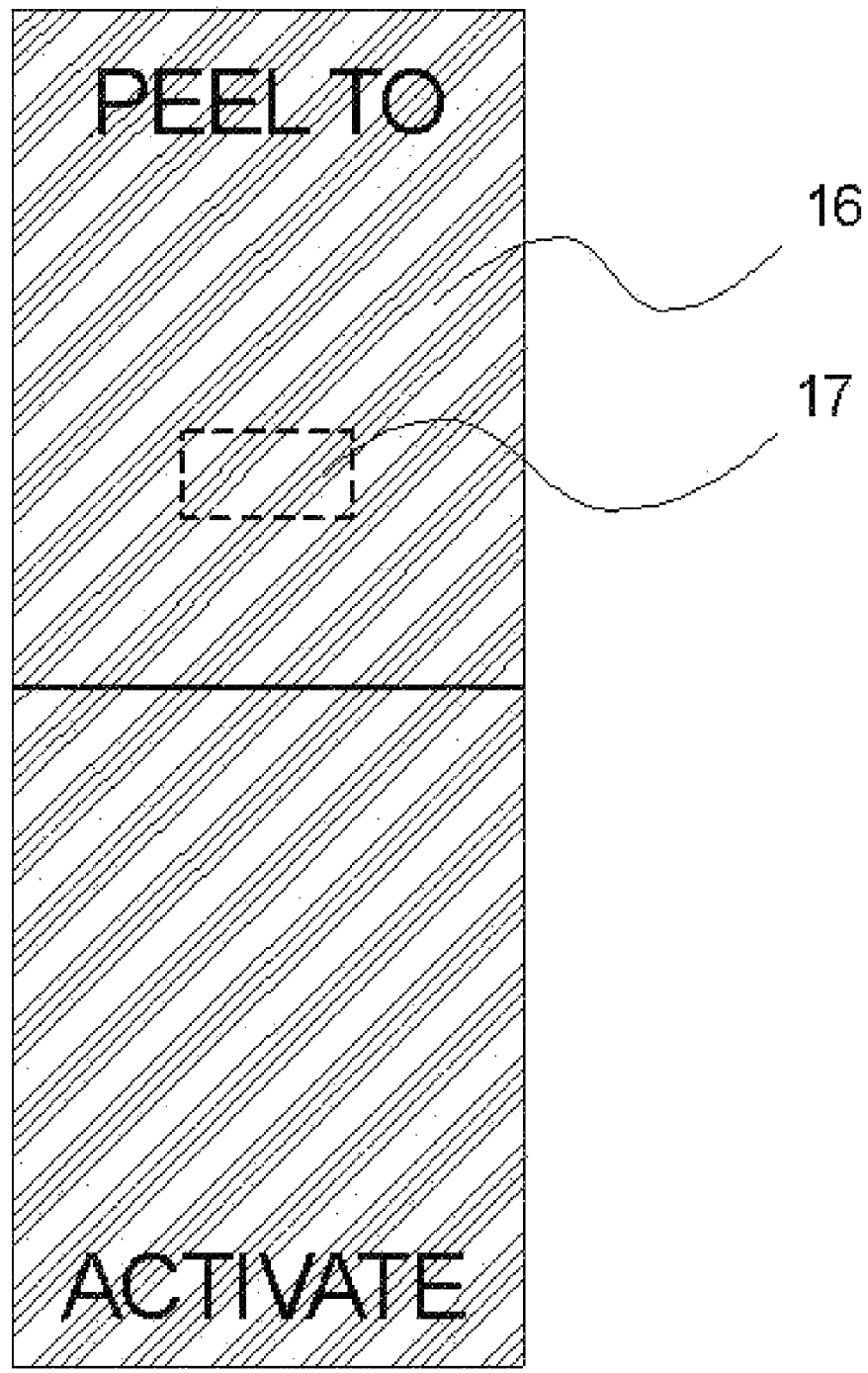
Figure 11:
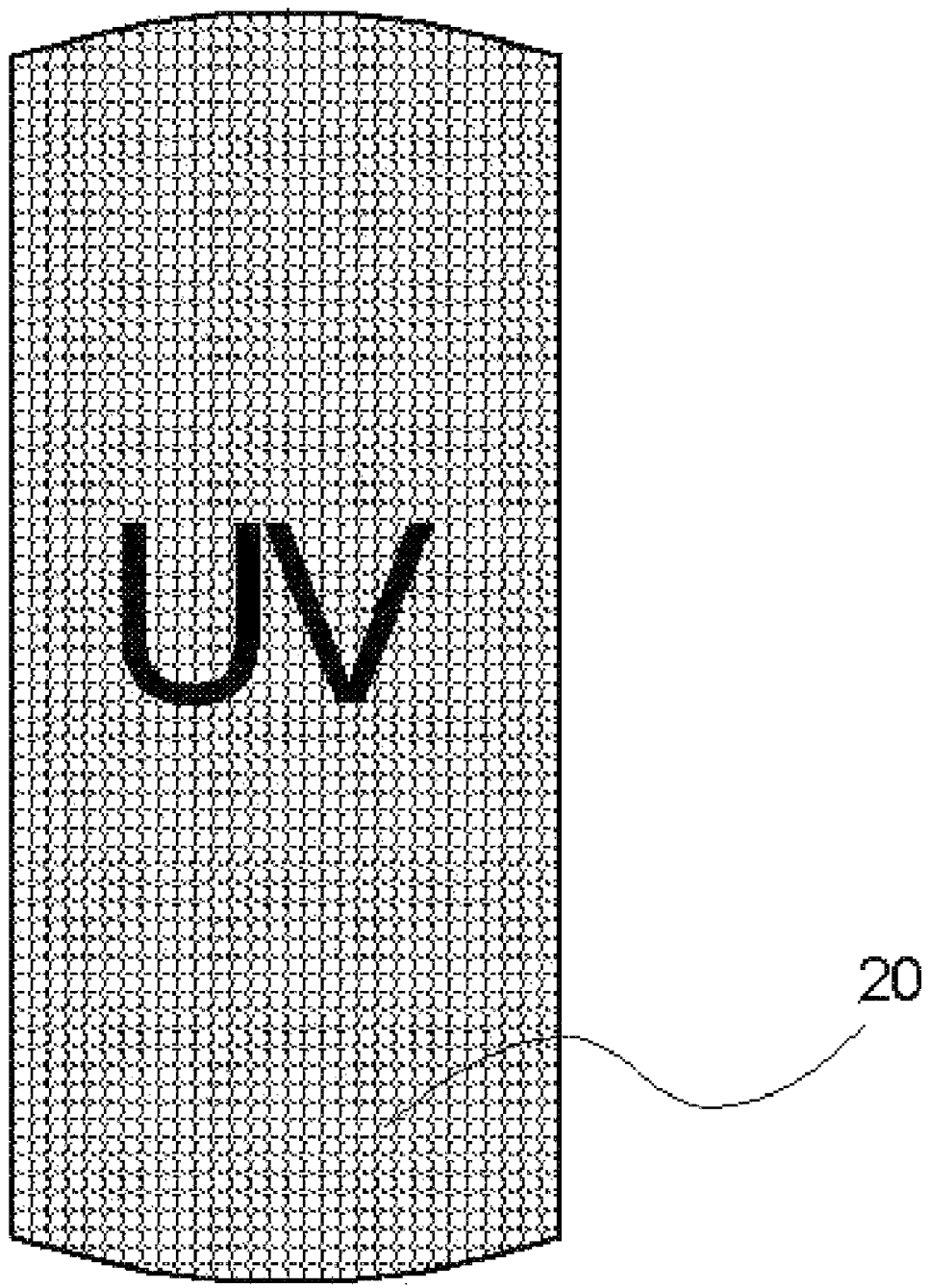
Figure 12:
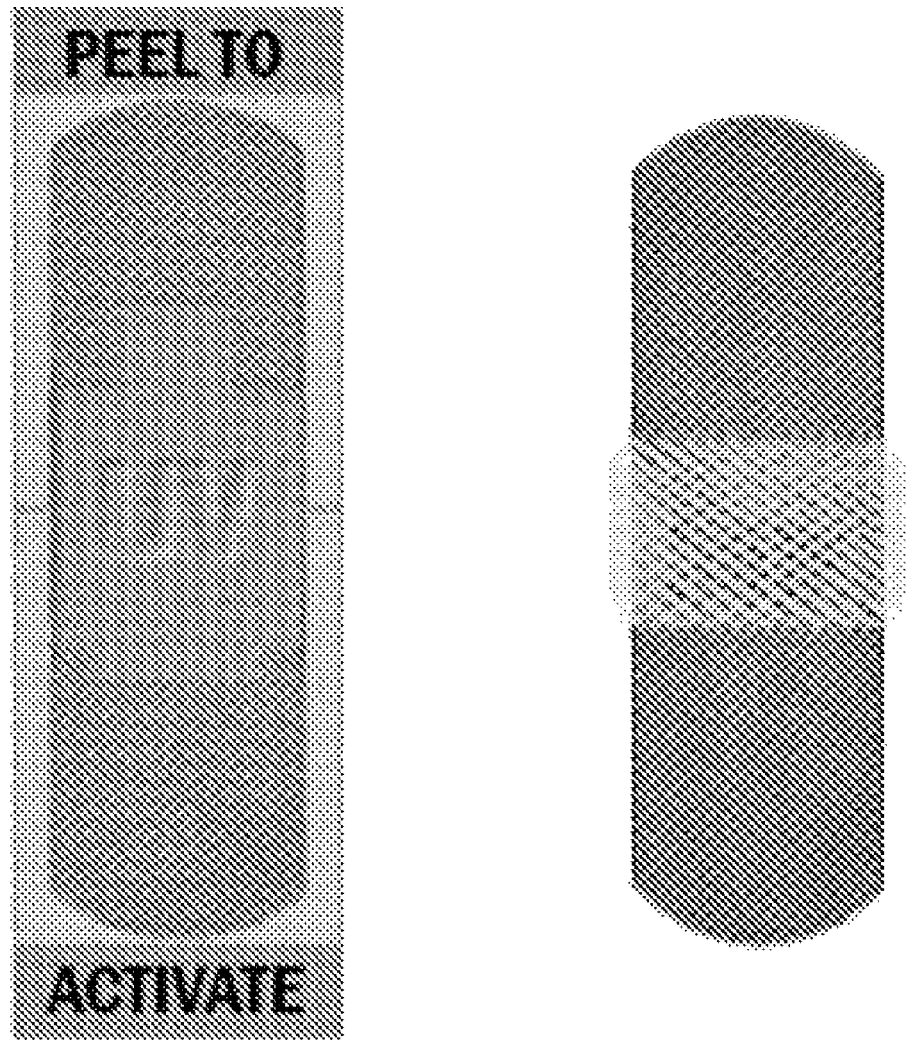

FIG. 1 Fiber Optic Interwoven Bandage Front
FIG. 2 LED Chip Embedded Bandage Front
FIG. 3 Fiber Optic Interwoven Bandage Side
FIG. 4 LED Chip Embedded Bandage Side
FIG. 5 Fiber Optic Interwoven Absorbent Pad Side
FIG. 6 LED Chip Embedded Absorbent Pad Side
FIG. 7 Optical Fiber Interwoven Perforated Thin Film
FIG. 8 LED Chip Embedded Perforated Thin Film
FIG. 9 LED Illuminated Fiber Optic Mesh
FIG. 10 Peel Off Backing
FIG. 11 Outer Cover
FIG. 12 Non Line Drawing Of Complete Bandage

DRAWINGS

Reference Numerals

10 LED
11 Battery
12 Timer
13 Magnetically Activated Switch
14 Electronic Relay
15 Flexible Circuit Board
16 Peel Off Backing
17 Magnetic Triggering Material
18 Absorbing Material
19 Non-Stick Thin Film
20 Outer Cover
21 Fiber Optic Strand
22 Adhesive
23 Micro Lens
24 Perforation

BACKGROUND OF THE INVENTION

The bandage parent application disclosed a Band-Aid type self-adhesive bandage in which LEDs back light the absorbent pad. However the cotton gauze absorbent pad material shaded the surface.

The applicant had worked with side emitting fiber while designing his toothbrush product (application Ser. No. 11/426,066 claim 15, application Ser. No. 13/023,665 claim 20) and embedding LED chips while designing his shoe product (application Ser. No. 12/198,310 claim 6).

In innovating the original bandage design by interweaving side emitting fiber optic strands or embedding LED chips into the absorbent pad outer surface the aforementioned critical issue is resolved.

DETAILED DESCRIPTION

FIGS. 1-12

FIG. 1 shows the front of the fiber optic interweaved embodiment of the bandage with the peel off backing removed. The absorbent pad is shown in the middle of the bandage with a perforated non-stick thin film 19 as the outer surface. Perforations 24 are shown dispersed uniformly on the film. The fiber optic strands 21 are shown interweaved into the absorbent pad surface. The magnetically activated switch 13 is shown embedded in the bandage above the absorbent pad. The LED 10 embedded in the bandage is shown just below the absorbent pad and is shown illuminating the optical fibers 21. Battery 11 timer 12 and relay 14 are also shown below the absorbent pad and are embedded in the bandage. All electronic circuitry is traced onto flexible circuit board 15. The entire circuit board is thin and flexible and embedded in the bandage.

FIG. 2 shows the front of the embedded LED chip embodiment of the bandage with the peel off backing removed. The battery 11 timer 12 magnetically activated switch 13 and relay 14 are shown in the same position as in FIG. 1. The LED chips 10 are shown wired directly to the output of relay 14

FIG. 3 shows a side cutout view of the fiber optic interweaved embodiment of the bandage with the peel off backing 16 detached. Embedded magnetic material 17 is shown embedded in the peel off backing 16. This material faces magnetically activated switch 13 embedded in the bandage. Non-stick thin film 19 is shown as the outer surface of the absorbent pad and perforations 24 are shown throughout the film. Just below the outer surface are shown the fiber optic strands 21. Under the strands is the absorbing material 18. LED 10 battery 11 timer 12 and relay 14 are shown on flexible circuit board 15. This board is embedded in the bandage and covered by outer cover 20 shown detached. Adhesive 22 is shown on the non-absorbent pad surfaces facing the peel off backing.

FIG. 4 shows a side cutout view of the embedded LED chip embodiment of the bandage with the peel off backing 16 detached. Location of battery 11 timer 12 magnetically activated switch 13 and relay 14 are the same as in FIG. 3. Absorbing material 18 is shown below perforated non-stick thin film 19 and embedded LED chips 10.

FIG. 5 shows a side cutout view of the fiber optic interweaved embodiment of the absorbent pad. Non-stick thin film 19 is shown as the outer surface with perforations 24 throughout. Fiber optic strands 21 are shown just below for clarity. These strands can be interweaved directly into non-stick thin film 19. Absorbing material 18 is shown below the surface. In this configuration the fiber optic strands 21 illuminate the perforated non-stick thin film 19 without the light being shaded by absorbing material 18.

FIG. 6 shows a side cutout view of the embedded LED chip embodiment of the absorbent pad. Perforated non-stick thin film 19 is again shown as the outer surface. A series of LED chips is shown just below the surface for clarity. These chips may be embedded into surface 19. Absorbing material 18 is again shown below the perforated surface 19 and LEDs 10.

FIG. 7 shows non-stick thin film 19 with fiber optic strands 21 interweaved. Perforations 24 are shown dispersed throughout the film. Fiber optic strands 21 are shown placed as to not block the perforations 24. LED 10 is shown illuminating the fiber optic strands 21 through micro lens 23. The micro lens 23 diffuses the light from LED 10 evenly into all the fiber optic strands 21. Both the LED 10 and micro lens 23 are embedded in the bandage.

FIG. 8 shows non-stick thin film 19 with embedded LED chips 10. The LEDs are shows positioned so as to not block perforations 24. The LED chips may be embedded in a flexible polycarbonate material or flexible polymeric sapphire composite material.

FIG. 9 shows an LED illuminated fiber optic mesh. This mesh is made up of optical fibers 21. It is illuminated by LED 10 through micro lens 23. This mesh can be placed directly over a cotton gauze absorbent pad and act as the sanitizing outer surface.

FIG. 10 shows the peel-off backing 16. The "Peel To Activate" instructions are shown printed on the backing. The magnetic triggering material 17 is shown embedded in the backing. This backing may be made from a treated paper material.

FIG. 11 shows the outer cover 20. This cover can be opaque to hide all the electronics. The designation "UV" is shown embossed on the cover. The outer cover may be made from medical cloth embedded with nylon fibers or a solar cell fabric. The adhesive 22 which secures it to the skin may be an epoxy.

FIG. 12 shows a non-line drawing embodiment of the complete bandage. On the left is the bandage prior to the removal of the peel-off backing. On the backing are printed the instructions "Peel To Activate". On the bandage outer cover is embossed "UV". On the right is the bandage after the peel-off backing is removed. The hue of light can be discerned on the absorbent pad surface.

DETAILED DESCRIPTION

Operation

The proposed bandage is intended to perform the same as an ordinary Band-Aid type bandage with the added benefit of a light infused photodynamically sanitized absorbent pad outer surface. This added benefit can be indicated to the consumer by imprinting the bandage or the bandage wrapper or packaging with "UV". The standard absorbency performance of a bandage is maintained.

Once the bandage is removed from its packaging or wrapper it would be applied normally. The light infusion function would be automatic. This function can be initiated by the removal of the peel-off backing. This enables the bandage to potentially sanitize against airborne pathogens during application.

Once applied a preset timing algorithm or cascaded timers can be used to maintain a sanitized surface or for sanitizing the wound surface or to treat subcutaneous infections. Cutaneous phototherapy functions such as pain management can be integrated using various wavelengths.

Two disinfection theories are proposed. The first is UVGI whereby deep UV wavelengths within or near the UVC band of the ultraviolet spectrum are used. Light at these wavelengths damages the DNA of microorganisms preventing them from reproducing and effectively inactivating them.

The other is the use of violet or blue light at or near 405 nm which excites molecules specifically within staph bacteria and inactivates it. A combination of wavelengths is feasible.

The proposed bandage can come in several sizes and shapes for specific uses such as surgical bandages.

Once applied the photodynamic function can continue for a predetermined time period of, for instance, 24 hours and this time period may be indicated to the consumer on the packaging or outer cover.

Once the need or function of the bandage expires it may be removed normally and disposed of in a manner consistent with that of ordinary bandages.

The applicant's startup company Germtron is currently developing this product.

I claim:

1. A simultaneously exudate absorbing and photodynamically wound sanitizing absorbent non-stick bandage comprising: a self-adhesive bandage having an integral absorbent pad with a perforated non-stick outer surface or meshed non-stick outer surface, LED illuminated side emitting fiber optic strands or LEDs embedded in said surface, a DC power source on board the bandage coupled to the LEDs and operable to provide power to the LEDs, wherein upon activation said surface emits light which effectively sanitizes a wound surface; a peel off backing containing embedded magnetic material which when pulled off activates a magnetically activated switch in the bandage initiating an illumination cycle; wherein electronic circuitry is traced on a circuit board embedded in the bandage; wherein a time of activation is controlled by a digital timer on said circuit board; and wherein said digital timer is a microprocessor controller with a preprogrammed timing algorithm.

2. The bandage in claim 1 wherein the outer surface is a thin film.

3. The bandage in claim 1 wherein the outer surface is wavelength specific transmissive polytetrafluoroethylene, PTFE.

4. The bandage in claim 1 wherein the absorbent pad comprises cotton.

5. The bandage in claim 1 wherein the LEDs comprise LED chips embedded in the outer surface that have a miniature lamp configuration.

6. The bandage in claim 1 wherein the LEDs comprise LED chips embedded in the outer surface that have a printed LED configuration.

7. The bandage in claim 1 wherein the LEDs comprise LED chips embedded in polycarbonate material.

8. The bandage in claim 1 wherein the LEDs comprise LED chips embedded in a polymeric sapphire substrate composite material.

9. The bandage in claim 1 wherein the LEDs emit at a wavelength within or near the germicidal UVC band of the ultraviolet spectrum.

10. The bandage in claim 1 wherein the LEDs emit at a molecule excitation frequency within the blue light spectrum at or near 405 nm.

11. The bandage in claim 1 wherein the DC power source is an ultra-thin flexible battery on said circuit board.

12. The bandage in claim 1 wherein irradiation is digitally pulsed.

13. The bandage in claim 1 wherein instructions "Peel To Activate" are printed on said backing.

14. The bandage in claim 1 wherein the peel off backing acts as a mechanical battery pullout tab.

15. The bandage in claim 1 wherein a moniker "UV" is imprinted or embossed on the bandage.

16. The bandage in claim 1 further comprising an outer cover that is a solar cell fabric acting as an adjunct or primary power source.

17. The bandage in claim 1 wherein light is propagated through the absorbent pad via a light guide.

18. The bandage in claim 1 wherein one or more absorbent pad components are coated with a reflective material.

19. The bandage in claim 1 wherein the bandage is disposed of after use.

20. The bandage in claim 1 wherein some or all of the elements on the circuit board are recyclable or reusable.

* * * * *